US008387497B2

(12) United States Patent
Raidel et al.

(10) Patent No.: US 8,387,497 B2
(45) Date of Patent: Mar. 5, 2013

(54) EXTENSIBLE ABSORBENT LAYER AND ABSORBENT ARTICLE (75) Inventors: Maria Raidel, Fuerth (DE); Franz Aschenbrenner, Kastl (DE); Jan Ullmann, Nuremberg (DE)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 283 days.

(21) Appl. No.: 12/696,637

(22) Filed: Jan. 29, 2010

(65) Prior Publication Data

US 2010/0126321 A1    May 27, 2010

Related U.S. Application Data

(62) Division of application No. 11/302,719, filed on Dec. 14, 2005, now abandoned.

(51) Int. Cl.
*B26F 1/24*  (2006.01)
*B26D 7/00*  (2006.01)
(52) U.S. Cl. .................... 83/30; 83/13; 83/648
(58) Field of Classification Search ............ 83/13, 648, 83/863, 861, 864, 862, 865, 343, 663, 30; 30/401; 616/383, 385.101; 156/268, 201, 156/202, 204, 216, 227, 257, 270, 308.2
See application file for complete search history.

(56) References Cited

U.S. PATENT DOCUMENTS

| | | | |
|---|---|---|---|
| 3,095,878 A * | 7/1963 | Bassett ........................ 604/366 |
| 3,338,992 A | 8/1967 | Kinney |
| 3,341,394 A | 9/1967 | Kinney |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,015,306 A * | 4/1977 | Fenster ........................ 15/209.1 |
| 4,074,599 A * | 2/1978 | Allen ................................ 83/346 |
| 4,100,324 A | 7/1978 | Anderson et al. |
| 4,166,464 A | 9/1979 | Korpman |
| 4,294,240 A * | 10/1981 | Thill ................................ 602/21 |
| 4,340,563 A | 7/1982 | Appel et al. |
| 4,389,211 A | 6/1983 | Lenaghan |
| 4,494,278 A | 1/1985 | Kroyer et al. |
| 4,589,876 A | 5/1986 | Van Tilburg |
| 4,610,189 A | 9/1986 | Lombardo |
| 4,613,321 A * | 9/1986 | Kesten et al. ................. 493/342 |
| 4,640,810 A | 2/1987 | Laursen et al. |
| 4,676,784 A | 6/1987 | Erdman et al. |
| 4,753,843 A * | 6/1988 | Cook et al. ..................... 442/333 |

(Continued)

FOREIGN PATENT DOCUMENTS

EP         0 336 578 B1    1/2001
WO    WO 2004/098328 A1   11/2004

OTHER PUBLICATIONS

Manson, John A. and Leslie H. Sperling, "Bicomponent and Biconstituent Fibers," *Polymer Blends and Composites*, Plenum Press, New York, Section 9.2, 1976, pp. 273-277.

*Primary Examiner* — Ghassem Alie
(74) *Attorney, Agent, or Firm* — R. Joseph Foster, III (57) ABSTRACT

The present invention provides a method of preparing an absorbent layer from an absorbent nonwoven web having a first plurality of slits with a first orientation and a second plurality of slits with a second orientation, wherein the first orientation is different from the second orientation. The first plurality of slits and the second plurality of slits are at least partially through the absorbent nonwoven web, and the second plurality of slits at least partially intersects the first plurality to form apertures in the absorbent nonwoven web.

5 Claims, 7 Drawing Sheets

U.S. PATENT DOCUMENTS

| | | |
|---|---|---|
| 4,848,464 A | 7/1989 | Jennings, Jr. et al. |
| 4,950,264 A | 8/1990 | Osborn, III |
| 5,057,368 A | 10/1991 | Largman et al. |
| 5,069,970 A | 12/1991 | Largman et al. |
| 5,108,820 A | 4/1992 | Kaneko et al. |
| 5,108,827 A | 4/1992 | Gessner |
| 5,229,191 A * | 7/1993 | Austin ............................ 428/198 |
| 5,277,976 A | 1/1994 | Hogle et al. |
| 5,330,822 A | 7/1994 | Berg et al. |
| 5,336,552 A | 8/1994 | Strack et al. |
| 5,397,316 A | 3/1995 | Lavon et al. |
| 5,466,410 A | 11/1995 | Hills |
| 5,527,171 A | 6/1996 | Soerensen |
| 5,607,414 A | 3/1997 | Richards et al. |
| 5,611,790 A | 3/1997 | Osborn, III et al. |
| 5,658,269 A | 8/1997 | Osborn, III et al. |
| 5,713,884 A | 2/1998 | Osborn, III et al. |
| 5,804,021 A | 9/1998 | Abuto et al. |
| 5,868,724 A | 2/1999 | Dierckes, Jr. et al. |
| 5,925,299 A | 7/1999 | Dierckes, Jr. et al. |
| 6,203,654 B1 | 3/2001 | McFall et al. |
| 6,315,756 B1 | 11/2001 | Tankovich |
| 6,387,084 B1 | 5/2002 | VanGompel et al. |
| 6,703,537 B1 * | 3/2004 | Roe et al. ....................... 604/369 |
| 7,005,558 B1 | 2/2006 | Johansson et al. |
| 2006/0047257 A1 | 3/2006 | Raidel et al. |
| 2006/0058761 A1 | 3/2006 | Kudo et al. |
| 2007/0135787 A1 | 6/2007 | Raidel et al. |
| 2007/0299415 A1 * | 12/2007 | Poccia et al. .................... 604/367 |

\* cited by examiner

EXTENSIBLE ABSORBENT LAYER AND ABSORBENT ARTICLE

RELATED APPLICATION

This application is a divisional of application Ser. No. 11/302,719, entitled "Extensible Absorbent Layer and Absorbent Article" and filed in the U.S. Patent and Trademark Office on Dec. 14, 2005 now abandoned.

FIELD OF THE INVENTION

The present invention relates to disposable absorbent articles such as sanitary napkins, pantiliners or incontinence pads and absorbent layers used therein. The present invention further relates to a process of manufacturing an absorbent layer or absorbent article.

BACKGROUND OF THE INVENTION

Disposable absorbent articles, such as sanitary napkins worn by women, must fulfill numerous requirements in order to be considered satisfactory for use. From the standpoint of the consumer using the disposable absorbent article, efficient absorption and retention of liquid and other discharges from the human body must be provided, and possible soiling of the wearers body or the wearers garment should be avoided. In addition, the absorbent article should be comfortable for a user to wear. The absorbent article should therefore be able to individually conform to the shape of the wearers body, so that the wearer is not hindered by the absorbent article. Ideally, the absorbent article should not be perceived by the wearer at all when worn. On the other hand, the absorbent article should not be too soft and deformable, otherwise bunching, twisting or roping of the absorbent article or lumping of the absorbent layer may occur, when the article is worn. This would seriously deteriorate the performance of the absorbent article and influence negatively the wearing comfort. Furthermore, the absorbent article and especially the absorbent layer must have sufficient structural integrity to withstand the forces exerted onto the absorbent article when worn. At the same time, the absorbent article should be thin so that the absorbent article may be worn in an inconspicuous manner. From the manufacturer's point of view, the materials used to produce the absorbent article must be suitable for mass production at very high production rates. The materials used to produce the absorbent article must therefore be easily obtained and be of relatively low cost. Furthermore, the materials must be easily processed at high speeds, which often include considerable forces and tensions being applied to the material, especially in the machine direction.

In order to increase the wearing comfort of sanitary napkins it has been suggested in the art to provide these articles with stretchability or increased flexibility. One method suggested in the art is to provide slits in the materials used to form the absorbent article. Excessive extensibility of an absorbent layer in the longitudinal direction, which is generally the machine direction, will make it very difficult to prepare such an absorbent layer on a production line designed for very high production rates (high speeds). Furthermore, for the absorbent article to be able to conform to the body of the wearer, the absorbent layer should be sufficiently extensible in both the longitudinal and lateral direction, while maintaining sufficient strength in both directions. At the same time, care must be taken not to significantly reduce the flexural resistance of the absorbent article. If the flexural resistance is reduced too much, the absorbent article will bunch, twist or rope or form lumps when the article is worn. Additionally, the articles might not be accepted by the consumer if the absorbent article feels too flexible, i.e. flimsy or flabby, thereby creating the impression that the article will not provide sufficient protection against the soiling of the garment to be protected. Furthermore, care should be taken that the formation of slits in the absorbent layer does not impair the efficiency of liquid intake, liquid distribution and liquid retention, due to the quick passage of liquid through the absorbent layer via the cuts or apertures formed therein.

A current trend in feminine hygiene products is to provide these products with aesthetic features such as colors, apertures and embossing to provide the consumer with a sense that the feminine hygiene products will be effective in absorbing bodily fluids. Color can be used to show the consumer or user that the product has new features, absorbency, and leakage protection.

There is a need in the art to provide an absorbent article which is extensible and highly conformable to the body of the wearer, while at the same time maintaining sufficient structural strength to avoid bunching, twisting or roping and the formation of lumps. In addition, there is a need in the art to make efficient usage of the absorbent capacity of the absorbent layer, and having the ability to produce the absorbent layer at high production rates (high speeds) at relatively reasonable or low cost. In addition, there is a need to provide additional color or features to absorbent products and to provide a way to convey these additional features to the consumer or user of these products.

SUMMARY OF THE INVENTION

The present invention provides an absorbent article which is extensible and highly conformable to the body of the wearer. Furthermore, the present invention provides an extensible and highly conformable absorbent layer for an absorbent article which efficiently utilizes the absorbent capacity of the absorbent layer. The present invention solves the above outlined problems by providing an absorbent article, an absorbent layer for use in an absorbent article, and a process for manufacturing the absorbent layer. Further embodiments and features of the different aspects of the present invention become apparent in the detailed description and the figures appended thereto.

The absorbent article of the present invention has a longitudinal direction and a lateral direction. In addition, the absorbent article has a top layer, a backing layer, and an absorbent layer positioned between the top layer and the backing layer. The absorbent layer is prepared from an absorbent nonwoven web having a first plurality of slits with a first orientation and a second plurality of slits with a second orientation, wherein the first orientation is different from the second orientation. The first plurality of slits and the second plurality of slits are at least partially through the absorbent nonwoven web, and the second plurality of slits at least partially intersects the first plurality of slits in a manner such that where the first and second plurality of slits intersect the first and second plurality of slits combine to form apertures in the absorbent nonwoven web. The first plurality of slits may be non-linear and the second plurality of slits may also be non-linear.

In further embodiments of the present invention, the top layer of the absorbent article may be a liquid-permeable material and the bottom layer may be a liquid-impermeable material. In addition, the basis weight of the absorbent nonwoven web may be between about 20 g/m² and 1000 g/m². Further, the basis weight of the absorbent nonwoven web may be between about 50 g/m² and 500 g/m² and generally between about 70 g/m² and 250 g/m².

In yet a further embodiment of the present invention, the first plurality of slits may be non-linear. Likewise, the second plurality of slits may also be non-linear. Each non-linear slit has an effective length in longitudinal direction in the range between about 2 mm and about 20 mm and an effective length in lateral direction in the range between about 0.5 mm and about 10 mm.

In another embodiment of the present invention, provided is an absorbent nonwoven web having a first plurality of slits with a first orientation and a second plurality of slits with a second orientation, wherein the first orientation is different from the second orientation. The first plurality of slits and the second plurality of slits are at least partially through the absorbent nonwoven web, and the second plurality of slits at least partially intersects the first plurality of slits in a manner such that where the first and second plurality of slits intersect the first and second plurality of slits combine to form apertures in the absorbent nonwoven web.

In another embodiment of the present invention, provided is a process for preparing a web, in particular the absorbent nonwoven web of the absorbent layer of the present invention. In this embodiment, the process has the steps of a) providing a web; b) providing a slitting apparatus having anvil roll, a first cutting roll and a second cutting roll; c) passing the web between the first cutting roll and the anvil to form a first plurality of slits in the absorbent nonwoven web; and d) passing the web between the second cutting roll and the anvil to form a second plurality of slits in the absorbent nonwoven web, wherein at least one slit in the second plurality of slits intersects at least one slit from the first plurality of slits such that an aperture is formed in the web. In the process of the present invention, both the first and second cutting rolls are positioned adjacent the same anvil roll. That is, the first cutting roll and the second cutting roll place slits in the absorbent nonwoven web against the same anvil roll. The absorbent nonwoven web of the present invention is brought into contact with the anvil roll, cut with the first cutting roll. Once cut or slitted with the first cutting roll, the web remains in contact with the anvil roll and is cut or slit with the second cutting roll. The first and second cutting rolls may be run in unison to register the first and second slits cut into the web.

In another embodiment of the present invention, provided is an apparatus for aperturing a web. The apparatus has an anvil roll, a first cutting roll and a second cutting roll, wherein the first cutting and second cutting rolls are in communication with the anvil roll. Each cutting roll has a series of protrusions that are capable of forming slits in a web passed between the anvil and each cutting roll. At least some of the protrusions of the first cutting roll and some of the protrusions of the second cutting roll are aligned on the anvil such that at least a portion of slits cut by the first cutting roll overlap at least a portion of the slits cut by the second cutting roll in the area where the slits overlap one another. In a further embodiment of the apparatus of the present invention, there may be at least one additional cutting roll in communication with the anvil. Each additional cutting roll has a series of protrusions that are capable of forming slits in a web passed between the anvil and each cutting roll. Each cutting roll may be run in unison with the anvil roll.

DEFINITIONS

As used herein with reference to the present invention, the term "disposable" includes being disposed after use and not intended to be washed and reused.

As used herein with reference to the present invention, the term "layer" when used in the singular can have the dual meaning of a single element or a plurality of elements.

As used herein with reference to the present invention, the term "liquid" means a non-particulate substance and/or material that flows and can assume the interior shape of a container into which it is poured or placed.

As used herein with reference to the present invention, the term "longitudinal" means having the longitudinal axis in the plane of the article and is generally parallel to a vertical plane that bisects a standing wearer into left and right body halves when the article is worn. The "lateral" axis lies in the plane of the article generally perpendicular to the longitudinal axis, i.e., so that a vertical plane bisects a standing wearer into front and back body halves when the article is worn.

As used herein, the term "machine direction" or "MD" means the length of a fabric in the direction in which it is produced. This direction as a rule essentially corresponds to the above defined longitudinal direction.

The term "cross machine direction", "cross direction" or "CD" means the width of fabric, i.e. a direction generally perpendicular to the MD. In line with the above definitions, the cross machine direction as a rule essentially corresponds with the lateral direction of the absorbent layer.

As used herein with reference to the present invention, the term "conjugate fibers" refers to fibers that have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat. No. 5,336,552 to Strack et al., and U.S. Pat. No. 5,382,400 to Pike et al., each of which is hereby incorporated by reference. For two component fibers, the polymers may be present in ratios of 75/25, 50/50, 25/75 or any other desired ratios. The fibers may also have shapes such as those described in U.S. Pat. No. 5,277,976 to Hogle et al., and U.S. Pat. Nos. 5,069,970 and 5,057,368 to Largman et al., each of which is hereby incorporated by reference, hereby incorporated by reference in their entirety, which describe fibers with unconventional shapes.

As used herein with reference to the present invention, the term "biconstituent fibers" refers to fibers that have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multi-constituent fibers. Fibers of this general type are discussed in, for example, U.S. Pat. No. 5,108,827 to Gessner, which is hereby incorporated by reference. Bicomponent and biconstituent fibers are also discussed in the textbook Polymer Blends and Composites by John A. Manson and Leslie H. Sperling, copyright 1976 by Plenum Press, a division of Plenum Publishing Corporation of New York, IBSN 0-306-30831-2, at pages 273 through 277.

As used herein with reference to the present invention, the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al, each of which is hereby incorporated by reference Spunbond fibers are generally not tacky when they are deposited onto a collecting surface. Spunbond fibers are generally continuous and have average diameters (from a sample of at least 10) larger than 7 microns, more particularly, between about 10 and 35 microns. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., each of which is hereby incorporated by reference and describe fibers with unconventional shapes.

As used herein with reference to the present invention, the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al, which is hereby incorporated by reference. Meltblown fibers are microfibers that may be continuous or discontinuous, are generally smaller than 10 microns in average diameter, and are generally tacky when deposited onto a collecting surface.

"Airlaying" is a known process by which a fibrous nonwoven layer can be formed. In the airlaying process, bundles of small fibers having typical lengths ranging from about 3 to about 52 millimeters are separated and entrained in an air supply and then deposited onto a forming screen, usually with the assistance of a vacuum supply. The randomly deposited fibers then are bonded to one another using, for example, hot air, a spray adhesive, or a binder. Examples of airlaying technology can be found in U.S. Pat. Nos. 4,494,278 to Kroyer; 5,527,171 to Soerensen; and 4,640,810 to Laursen, each of which is hereby incorporated by reference. The term "airlaid fiber layer" as used herein with reference to the present invention relates to layers obtained by means of an airlaying process.

As used herein with reference to the present invention, the term "coform" means a process in which at least one meltblown die head is arranged near a chute through which other materials are added to the web while it is forming. Such other materials may be pulp, superabsorbent or other particles, natural polymers (for example, rayon or cotton fibers) and/or synthetic polymers (for example, polypropylene or polyester) fibers, for example, where the fibers may be of staple length. Coform processes are shown in commonly assigned U.S. Pat. No. 4,818,464 to Lau and U.S. Pat. No. 4,100,324 to Anderson et al. each of which is hereby incorporated by reference. Webs produced by the coform process are generally referred to as coform materials.

"Carded web" refers to webs that are made from staple fibers that are sent through a combing or carding unit, which opens and aligns the staple fibers in the machine direction to form a generally machine direction-oriented fibrous nonwoven web. The web is then bonded by one or more of several known bonding methods. Bonding of nonwoven webs may be achieved by a number of methods; powder bonding, wherein a powdered adhesive or a binder is distributed through the web and then activated, usually by heating the web and adhesive with hot air; pattern bonding, wherein heated calendar rolls or ultrasonic bonding equipment are used to bond the fibers together, usually in a localized bond pattern, though the web can be bonded across its entire surface if so desired; through-air bonding, wherein air which is sufficiently hot to soften at least one component of the web is directed through the web; chemical bonding using, for example, latex adhesives that are deposited onto the web by, for example, spraying; and consolidation by mechanical methods such as needling and hydroentanglement.

"Superabsorbent" refers to a water-swellable, water-insoluble organic or inorganic material capable, under the most favorable conditions, of absorbing at least about 10 times its weight and, more desirably, at least about 15 times its weight in an aqueous solution containing 0.9 weight percent sodium chloride. The superabsorbent materials can be natural, synthetic, and modified natural polymers and materials. In addition, the superabsorbent materials can be inorganic materials, such as silica gels, or organic compounds such as cross-linked polymers. A material is "absorbent" if it absorbs at least five times its weight of the aqueous solution under these conditions.

"Personal care product" means diapers, training pants, absorbent underpants, adult incontinence products, swim wear, bandages and other wound dressings, and feminine hygiene products.

"Feminine hygiene products" means sanitary napkins, pads, and pantiliners.

"Target area" refers to the area or position on a personal care product where an insult is normally delivered by a wearer.

DETAILED DESCRIPTION OF THE INVENTION

In the following the present invention will be described especially with reference to sanitary napkins but is not limited to sanitary napkins. It is also applicable to other absorbent articles such as personal care products, including diapers, incontinence pads, pantiliners, disposable swimwear, training pants and the like.

Figure 1:
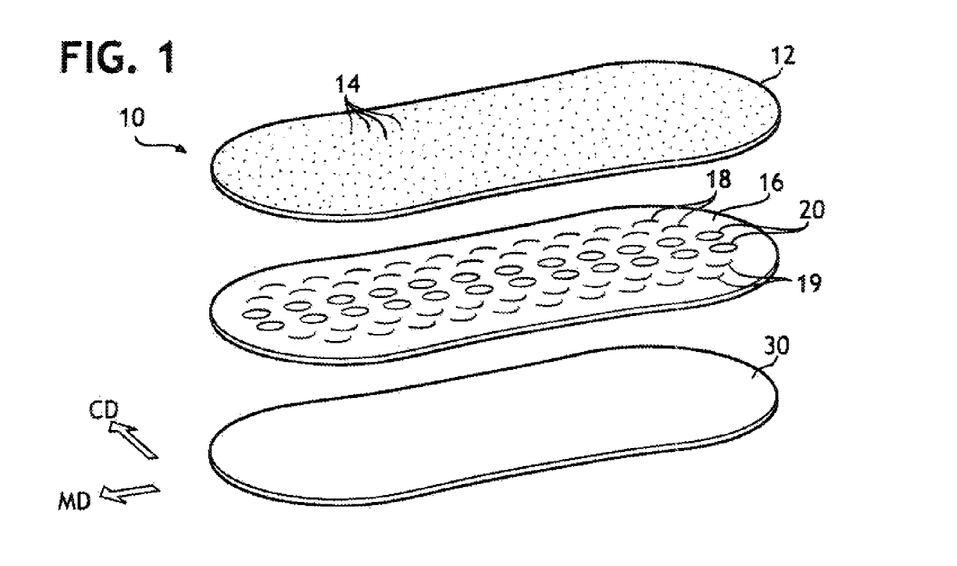
FIG. 1 is an exploded view of a first embodiment of an absorbent article according to the present invention.
Figure 2:
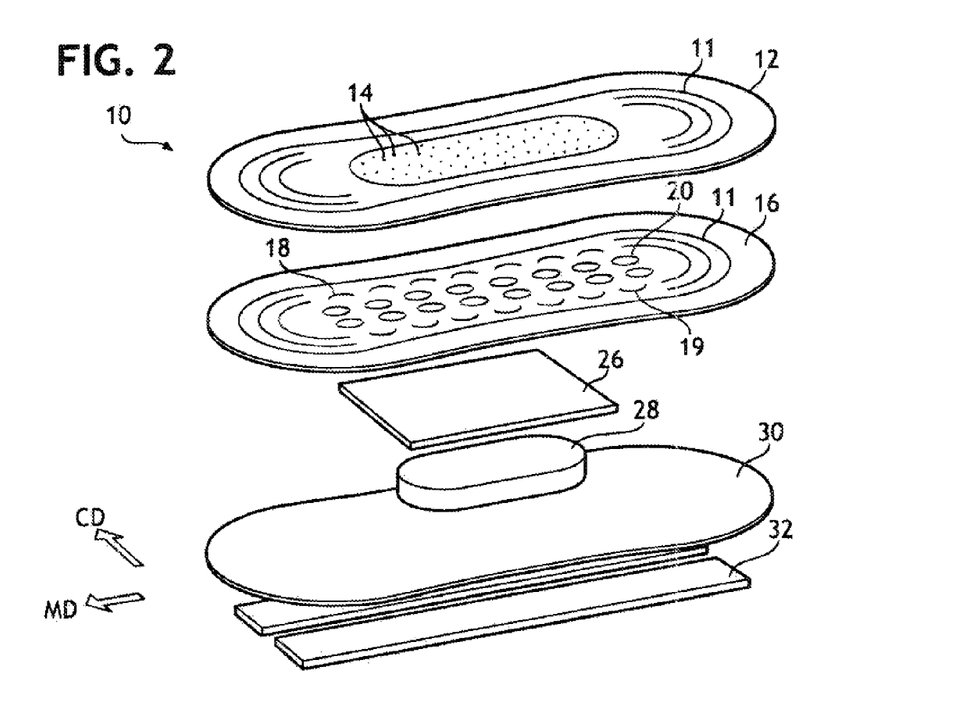
FIG. 2 is an exploded view of a second embodiment of an absorbent article according to the present invention.

FIG. 1 and FIG. 2 show two embodiments of the absorbent article 10 according to the present invention. It is to be understood within the present application that all figures show selected embodiments comprising one or more aspects of the present invention and that the embodiments shown in these figures are non-limiting embodiments by means of which selected properties or selected components or features of the absorbent articles are demonstrated. The absorbent article according to the present invention has a longitudinal direction, corresponding to the machine direction MD, and a lateral direction, corresponding to the cross machine direction CD. The cross machine direction is perpendicular to the machine direction. The absorbent articles 10 comprise a top layer 12, wherein the top layer 12 may optionally have extensibility in lateral direction of at least 30% to 70% at 4N/50 mm. The tensile strength of the top layer material can be determined following the procedures outlined in the tensile test on strips of textile fabrics of DIN 53 857 on a strip of material having a width of 50 mm and measured without a pre-load force. The top layer 12 is the layer facing the wearer's body when the absorbent article is in use. Desirably, the top layer 12 is a liquid permeable material. The top layer 12 can be made of a material that permits the passage of fluid without drawing the fluid horizontally in parallel to the top layer to any great extent. In addition, the top layer should retain little or no fluid in the structure, so that a relatively dry surface is provided next to the wearer's skin. In general, the top layer is a single layer of a material with a width sufficient to cover the surface of an absorbent layer positioned underneath it. The top layer 12 preferably extends to the longitudinal edges of the absorbent article and is bonded to a backing layer 30. The top layer 12 may be bonded to the backing layer 30 using any known method which does not leave any hard or uncomfortable residues that would annoy the wearer. Those skilled in the art are familiar with methods of bonding the various materials and for bonding other possible materials in the absorbent article according to the present invention, including the use of pressure-sensitive adhesives, hot-melt adhesives, two-sided adhesive sheets, ultrasonic welding and heat sealing, to name but a few. Adhesives such as hot-melt adhesives may be used uniformly or in the form of a continuous or non-continuous layer.

The top layer 12 may be manufactured from materials known in the art. Known materials include, for example, card weaves and spunbonded nonwovens made of polyester, polypropylenes, polyethylenes, nylon or other heat-bonded fibers. Other polyolefins such as copolymers of polypropylene and polyethylene, linear, low-density polyethylene fiber nonwovens which are finely perforated or mesh-like materials are also suitable. Other suitable materials include composite materials of polymers and nonwoven material. The composite layers are usually formed by extrusion of the polymer on a layer of spunbonded nonwoven to form an integral layer. These materials may contain pigments, such as titanium dioxide to improve the masking properties of the top layer 12 or other additives to improve the properties of the material, like substances improving the hydrophilic properties of the top layer, e.g. surfactants.

In a non-limiting embodiment of the absorbent article according to the present invention, the top layer 12 is made of a carded nonwoven web made of polypropylene fibers, which generally has a basis weight of from about 18 to about 40 $g/m^2$. In a specific embodiment, the basis weight is 27 $g/m^2$. Alternatively, the top layer 12 may be made of a spunbonded nonwoven made of polypropylene fibers and generally having a basis weight of from about 18 to about 40 $g/m^2$. Top layer 12 may comprise a multitude of perforations 14, which may be oval shaped, square shaped or circular shaped, or of any other suitable shape, in order to facilitate the uptake of liquid through the top layer, especially highly viscous components of such a liquid. The top layer may be completely perforated or may only be perforated in selected areas thereof. In the specific embodiment shown in FIG. 1, the perforations are formed throughout the surface of the top layer 12. In the embodiment shown in FIG. 2, the perforations 14 are only situated in the central area of the top layer 12, corresponding to the target area of the absorbent article. Generally, the perforations 14 could also be present within a central strip extending along the complete length of the absorbent article or uniformly distributed over the whole area of the top layer 12. The perforations may be arranged randomly or regularly in a pattern.

Alternatively, the liquid-permeable top layer 12 may also consist of a perforated film made from a liquid-impermeable material, such as polyethylene or polypropylene.

The top layer 12 may further comprise embossing lines 11, as shown in FIG. 2, for adapting the shape of the absorbent article to the shape of the wearer's body and to improve its conformability to the body of the wearer. Such embossing lines 11 can be formed using conventional techniques. If embossing lines 11 are present in the top layer 12, the underlying absorbent layer 16 will usually also comprise corresponding embossing lines because such embossing lines are usually formed in a single embossing step during the manufacturing of the absorbent article.

The absorbent articles 10 shown in FIGS. 1 and 2 further comprise a backing layer 30 laminated to the top layer 12, wherein the backing layer 30 may have a higher extensibility in lateral direction than in longitudinal direction. The extensibility in lateral direction may have a value of between at least 5% and 40% at 4N/50 mm as determined following the procedures of the tensile test on strips of textile fabrics outlined in DIN 53 857 on a strip of material having a width of 50 mm and measuring without a pre-load force. In an embodiment of the present invention, the backing layer is prepared from a liquid-impermeable material. The backing layer 30 may be made of any suitable material that is sufficiently liquid-impermeable and exhibits the required extensibility. The backing layer may for instance consist of a polymeric film having the desired extensibility. The backing layer 30 may allow atmospheric vapor and moisture to pass through the absorbent article while preventing body fluid from passing through. Suitable extensible materials are for instance mentioned in U.S. Pat. No. 4,166,464 to Korpman, the disclosure of which is fully incorporated herewith. Suitable polymer materials for use as the backing layer are, for instance, Kraton 1107, a thermoplastic elastomeric A-B-A (styrene-isoprene-styrene, S-I-S) copolymer or Solprene 420, which is also a S-I-S copolymer or mixtures thereof. Furthermore, a layer made of different types of polyethylene having different densities may be used. Additionally, micro-embossed polyethylene or polypropylene films or films of polyolefin foams may be used. The backing layer may also be a layer which may be prepared from a mixture of polyethylenes having different densities. In an alternative embodiment of the present invention, the backing layer may be liquid permeable, if the absorbent article is used in conjunction with another liquid impermeable material, such as, liquid impermeable pants.

Both the top layer 12 and the backing layer 30 may comprise wing sections (not shown) located at the longitudinal sides of the absorbent article. Such wing sections are commonly used in the art for attachment of sanitary napkins to the wearer's undergarment. Wings or flaps are known in the art and are described in U.S. Pat. No. 4,589,876 to Van Tilburg, which is hereby incorporated by reference. Flaps are also shown in other patents, for example, U.S. Pat. No. 6,387,084 issued to VanGompel et al., which is hereby incorporated by reference for its discussion of the flaps and flap attachment means and in its entirety. In one embodiment (not shown), one or more elastic elements are disposed along the sides to form a gasket with the body of the user. Elastic sides are known in the art, as is shown in U.S. Pat. No. 6,315,765 issued to Datta et al., which is hereby incorporated by reference for its discussion of the elastic sides and in its entirety. In one embodiment, the elastic elements are disposed between the top layer and the backing layer.

The absorbent articles according to the present invention further have an absorbent layer 16 positioned between the top layer 12 and the backing layer 30. The absorbent layer 16 is generally made of one or more materials which together are essentially absorbent, hydrophilic, compressible, adaptable and non-irritating for the skin of the wearer. Suitable materials are well known in the art and include, for example, various natural or synthetic fibers, cellulose fibers, regenerated cellulose or cotton fibers or a blend of cellulose and other fibers or polyethylene or polypropylene fibers, or biconstituent fibers. In a specific embodiment, polypropylene fibers may be used.

The absorbent structure 16 may also include superabsorbent material. Superabsorbent materials suitable for use in the present invention are known to those skilled in the art, and may be in any operative form, such as particulate form, fibers and mixtures thereof. Generally stated, the superabsorbent material can be a water-swellable, generally water-insoluble, hydrogel-forming polymeric absorbent material, which is capable of absorbing at least about 15, suitably about 30, and possibly about 60 times or more its weight in physiological saline (e.g. saline with 0.9 wt % NaCl). The superabsorbent material may be biodegradable or bipolar. The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers may be lightly crosslinked to render the material substantially water insoluble. Crosslinking may, for example, be by irradiation or covalent, ionic, Van der Waals, or hydrogen bonding. Suitable materials are available from various commercial vendors such as The Dow Chemical Company and Stockhausen, Inc. The superabsorbent material may suitably be included in an appointed storage or retention portion of the absorbent system, and may optionally be employed in other components or portions of the absorbent article. The superabsorbent material may be included in the absorbent layer or other fluid storage layer of the absorbent article of the present invention in an amount up to about 60% by weight. Typically, the superabsorbent material, when present, will be included in an amount of about 5% to about 40% by weight, based on the total weight of the absorbent layer.

Typically, the absorbent layer is an absorbent nonwoven web. Suitable nonwoven webs are those nonwoven webs which are moisture stable and wettable. By "moisture stable", it is meant a nonwoven web which does not lose its integrity when the nonwoven web becomes wetted by a fluid. Exemplary absorbent nonwoven webs include, for example, nonwoven webs of airlaid fiber layers, coform fiber layers, tissue layer meltblown fiber layers or laminates thereof and laminates of airlaid fiber layers, tissue layers, coform fiber layers or meltblown fiber layers or laminates thereof with a nonwoven support. In one embodiment of the present invention, the absorbent nonwoven web is an airlaid web or a coform web, or a laminate of an airlaid web or a coform web with a support nonwoven web. The absorbent layer 16 material will have a basis weight of between about 20 $g/m^2$ to about 1000 $g/m^2$. In another embodiment of the present invention, the basis weight of the absorbent layer may be between 50 $g/m^2$ and 500 $g/m^2$ and generally between about 70 $g/m^2$ and 250 $g/m^2$.

The nonwoven support used in the absorbent layer material may be a spunbond fiber layer made of polypropylene fibers and having a basis weight in the range of 10 to 40 $g/m^2$, desirably 10 to 25 $g/m^2$.

In a further embodiment of the present invention, the absorbent layer material may be a laminate of an airlaid fiber layer or coform fiber layer with a basis weight of 70 $g/m^2$ to 250 $g/m^2$ and a spunbond fiber layer with a basis weight in the range of 10 to 40 $g/m^2$, specifically 10 to 25 $g/m^2$. When using a laminated absorbent layer, the absorbent layer is usually arranged in the absorbent layer in such a manner that the support layer faces in the direction of the top layer, i.e. towards the wearer.

The absorbent layer material may be an airlaid material, comprising a mixture of at least 70 wt.-% cellulose fibers, from about 2 to 6 wt-% polyethylene powder, 5 to 25 wt-% bicomponent or conjugate fibers, and optionally up to 2 wt-% of a latex binder, wherein the sum of the weight percentages of the different components present in the material adds up to 100 wt-%. Alternatively, the absorbent layer material may be a coform material containing between 30 and 50 wt-% polypropylene and between 50 and 70 wt-% cellulose, wherein the sum of the weight percentages of the different components present in the material adds up to 100 wt-%. Specifically, the coform material may contain between 30 and 40 wt-% polypropylene and between 60 and 70 wt-% cellulose. In a further embodiment, the coform material contains 40 wt-% polypropylene and 60 wt-% cellulose. The absorbent material may further comprise additives to improve its properties, such as surfactants or the superabsorbent materials described above to improve the intake or overall absorbent capacity of the absorbent article, respectively.

The absorbent layer of the present invention is provided with a first plurality of slits 18 having a first orientation and a second plurality of slits 19 with a second orientation, wherein the first orientation is different from the second orientation. By "different orientation" it is meant that the pattern of the first plurality of slits is different in some aspect than the second plurality of slits, whether length, width, spacing, direction, shape, configuration, or location on the slitted surface or a combination of these properties, such that the pattern generated by the first plurality of slits is different from the pattern generated by the second plurality of slits. In addition, the first plurality of slits 18 and the second plurality of slits 19 are at least partially through the absorbent layer 16, and the second plurality of slits 19 at least partially intersects the first plurality of slits 18 in a manner such that where the first and second plurality of slits intersect the first and second plurality of slits combine to form apertures 20 in the absorbent layer 16.

The first plurality of slits may be linear or non-linear and the second plurality of slits may also be linear or non-linear. The only requirement is that the first and second plurality of slits must intersect, and the area of the absorbent layer where they intersect must have an aperture formed in the absorbent layer. In another embodiment of the present invention, there may be at least one additional plurality of slits having an orientation different from the first and second plurality of slits. Each of the additional plurality of slits intersects at least one of the first and second pluralities of slits, and where the pluralities of slits with different orientations intersect, there is at least one aperture formed in the absorbent layer. Generally, when there are just two pluralities of slits with different orientations, at least one of the pluralities of slits will need to be non-linear to form an aperture. However, where there are more than two pluralities of slits with different orientations, each of the pluralities of slits may be linear.

Figure 3A:
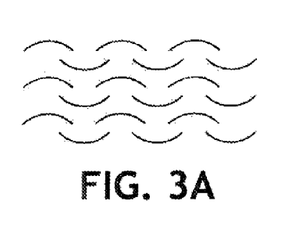
FIGS. 3A-F show possible arrangements for a plurality of slits in a pattern or orientation.
Figure 3B:
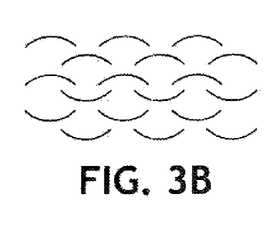
Figure 3C:
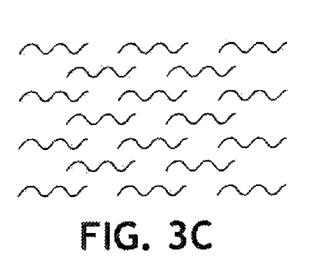
Figure 3D:
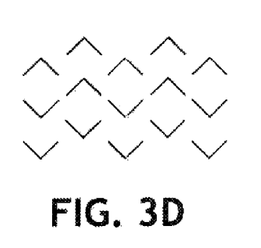
Figure 3E:
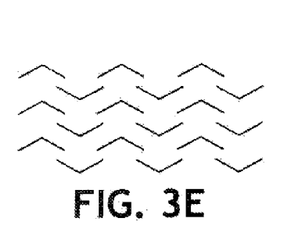
Figure 3F:
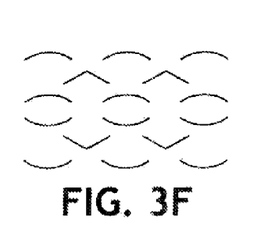

The orientation of the slits may vary greatly, as long as the slits have an effective component extending in the longitudinal direction and an effective component extending in the lateral direction. The non-linear slits of each plurality of slits may therefore be curved, for instance in the form of waves or arcs, as is shown in FIGS. 3A, 3B and 3C, or may have two or more linear sections extending in different directions, as is shown in FIGS. 3D and 3E or may be a combination of different curved slits and slits having two or more linear sections extending in different directions, as shown in FIG. 3F. In addition, the pattern of slits may have linear slits (not shown). In the present invention, the pattern of slits will be considered non-linear if one or more slits in the pattern are non-linear. The pattern of slits may be a repeating pattern, as shown in FIGS. 3A-3F, or may be a random pattern. Also, as shown in FIGS. 3A, 3B, 3D, 3E and 3F, not all of the slits in a plurality of slits need to have the configuration, orientation or shape. However, the second or any additional pattern of slits on the absorbent layer must intersect at least one of the first pattern of slits, such that an aperture is placed in the absorbent layer. This will be described in more detail below.

Figure 4:
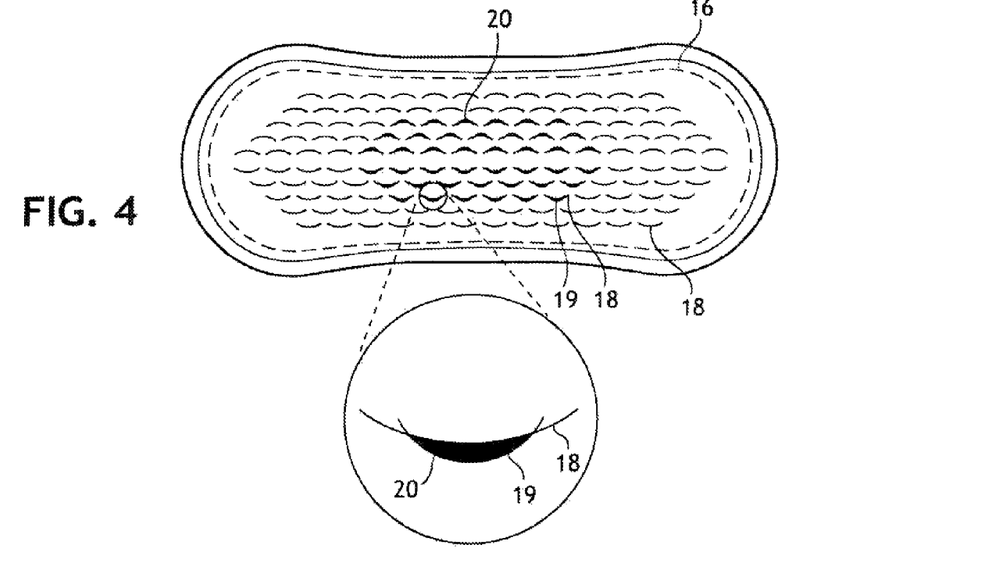
FIG. 4 shows an absorbent layer of the present invention with slits in a first orientation and slits in a second orientation that combine to form apertures.

Referring to FIG. 4, the first pattern of slits 18 in the absorbent layer 16 may be regularly arranged along a plurality of spaced apart lines 22 which extend in the direction parallel to the longitudinal direction, wherein these lines are spaced apart at a distance e. Two adjacent slits 18 arranged on one of these parallel lines are spaced apart by a distance c. Each slit 18 has an effective length a in longitudinal direction and an effective length d in lateral direction. The sum of the distance a and the distance c gives the length b along the longitudinal direction at which the slit-pattern along one parallel line 22 is repeated. The pattern of slits may either extend essentially over the complete surface of the absorbent layer or only selected sections thereof, for instance the central area of the absorbent layer or peripheral sections such as front and back sections and/or side sections. Generally, the effective length a of a slit in longitudinal direction can be selected to lie in the range between about 2 mm and about 20 mm. The effective length in cross direction d can be selected to lie in the range between about 0.5 mm and about 10 mm, specifically between about 1 mm and 6 mm. The ratio of the effective length a and the effective length d can be selected to lie in the range between 15:1 and 2:1, and, more specifically, in the range between 6:1 and 3:1. The distance e between each of the spaced apart parallel lines 22 can be selected to lie in the range between 4 mm and 8 mm, more specifically between 5 mm and 6 mm. The distance c between two adjacent slits in longitudinal direction can be selected to have a value in the range between 1 mm and 10 mm, specifically between 1 mm and 5 mm, more specifically between 1 mm and 3 mm. In addition the second plurality of slits and any additional plurality of slits cut into the absorbent layer may have these general dimensions.

Figure 5:
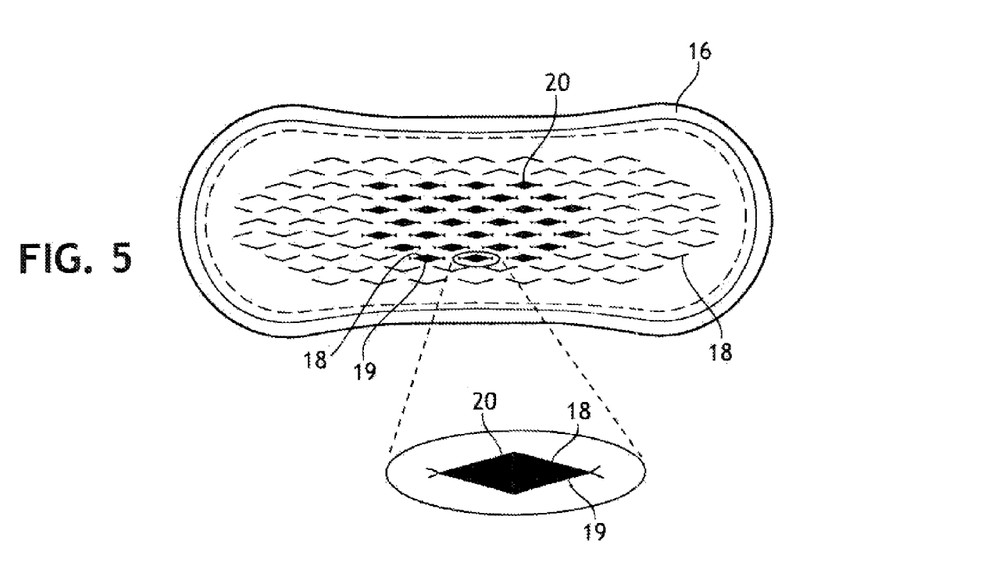
FIG. 5 shows an absorbent layer of the present invention with slits in a first orientation and slits in a second orientation that combine to form apertures.

A second plurality of slits 19 is cut into the absorbent layer 16, wherein at least one of the slits of the second plurality of slits 19 intersects at least one of the slits in the first plurality of slits 18. When the second plurality of slits 19 are cut into the absorbent layer and intersect the at least one of the first plurality of slits 18, the area of the absorbent layer between the intersecting slits is cut free from the absorbent layer, thereby forming an aperture 20 in the absorbent layer. In this regard, attention is directed to FIGS. 4 and 5, which show details of the intersecting slits from the first plurality of slits and the second plurality of slits. In FIG. 4, the second plurality of slits 19 may have the same or similar pattern with one or more aspects of the pattern being changed to form the apertures. For example the first and second plurality of slits may have the same shape or configuration but the second plurality of slits is out of phase or offset from the first plurality of slits 18. Other features of the slits may be changed to provide apertures in the absorbent layer 16. In the case of FIG. 4, as shown in the second plurality of slits 19, have a smaller arc radius than the arc of the first plurality of slits 18. In FIG. 5, the second plurality of slits 19 has the same general shape as the first plurality of slits 18, but is mirror images of one another.

Figure 6A:
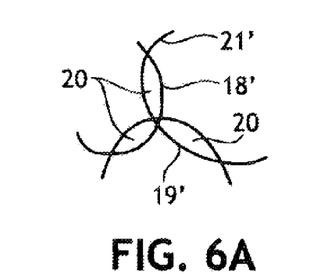
FIGS. 6A and 6B show a configuration of three slits which combine to form an aperture.
Figure 6B:
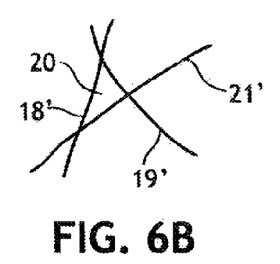

The intersection of the first and second pluralities of slits in FIGS. 4 and 5 are shown to be similar or inverted from one another, and this is not required by the present invention. One of or both of the plurality of slits may be linear; one may be arced and the other two linear lines together which form a non-linear slit and any other combination which allows for an aperture to be formed into the absorbent layer. In addition, more than two pluralities of slits that intersect can be used to form the apertures in the absorbent layer. For example, two possible configurations for forming an aperture using more than two intersecting pluralities of slits are shown in FIGS. 6A and 6B. For example, in FIG. 6A, three intersecting non-linear slits 18', 19' and 21' form the aperture 20. In FIG. 6B, three intersecting linear slits 18', 19' and 21' form the aperture 20. Any combination of linear and non-linear slits may be used to form the apertures in the absorbent layer 16.

The slitted and apertured absorbent layer used in the present invention should maintain a sufficient flexural resistance to avoid bunching of the absorbent layer, or formation of lumps therein when worn, or for it to be considered to be too flexible (flabby, flimsy) by the consumers. In specific embodiments of the present invention, the flexural resistance of the slitted absorbent layer is selected to have a value in the range of about 0.5 N to 1 N as determined by the circular bending procedure described, for instance, in European Patent EP 0336578 corresponding to U.S. Pat. No. 4,950,264 to Osborn, Ill., which is hereby incorporated by reference. Therein, the absorbent layer comprises a plurality of slits and apertures therethrough, and the ratio of the tensile strength of the absorbent layer in longitudinal direction and the tensile strength of the absorbent layer in lateral direction has a value in the range from 3.5:1 to 6:1. In specific embodiments of the present invention this ratio is selected to be in the range between 4.5:1 to 5.6:1.

To improve the extensibility of the absorbent layer while maintaining sufficient flexural resistance of the absorbent material, a pattern of non-linear slits and/or linear slits is cut or punched into the absorbent layer. The pattern of slits and apertures or linear slits which are at an acute angle relative to the longitudinal direction of the absorbent article should significantly decrease the tensile strength of the absorbent material in both the longitudinal direction (corresponding to the MD) and lateral direction (corresponding to the CD) while still maintaining sufficient stability and durability for the absorbent material to be processed at high speeds in a production line. At the same time, as already outlined above, the flexural resistance should not be decreased too much, otherwise the possibility of formation of lumps or bunching exists, or the absorbent article might be perceived by the consumer as being too flexible (flimsy, flabby). A reduction of the flexural resistance by between 40 and 70%, and more specifically by between 60 and 70%, compared to the non-slit material, is considered to be suitable.

In the present invention, the pattern formed by the first plurality of slits 18 may define a first and a second patterned area. The arrangement of the slits 18 in the second pattern area may be a mirror inverted image of the arrangement of the slits in the first pattern area. Such a pattern may for instance arise if one imagines a mirror plane extending along the middle of the absorbent layer in longitudinal direction and perpendicular to the surface of the flat absorbent layer and the pattern formed by the slits on one half of the absorbent layer being mirrored onto the second half of the absorbent layer. In a similar manner, the slits may be mirrored along the lateral center line in the lateral direction separately or in addition to the mirroring in the longitudinal direction. This is shown in FIGS. 4 and 5.

In the present invention, the second or optional additional pluralities of slits are cut in the absorbent layer, these second and optional additional plurality of slits are generally only cut in a portion of the absorbent layer where it is desired to have apertures on the absorbent layer. Stated another way, the second and additional slits are only provided in the absorbent layer to provide apertures and all of the remaining slits are part of the first plurality of slits. In the alternative, the first plurality of slits could be cut into the absorbent layer such that all of the slits having the exact same orientation or configurations. The second plurality of could be slits cut into the absorbent layer which mirror the first plurality of slits and intersect the first plurality of slits to form the apertures. The manner in which the slits are cut into the absorbent layer is not critical to the present invention, provided that the slits and apertures have the configurations described herein. It is noted, however, that the process of the present invention is highly advantageous for forming the slitted and apertured absorbent layer.

Figure 7:
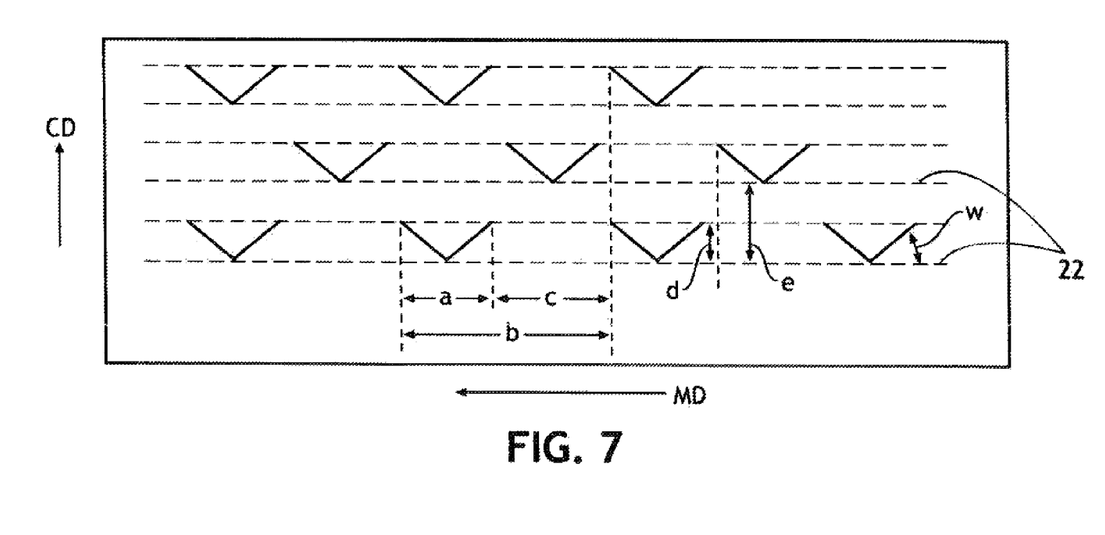
FIG. 7 shows a schematic representation of a section of a pattern of slits usable in the absorbent layer.

If the slits are nonlinear slits which are at an acute angle relative to the longitudinal direction of the absorbent article, the acute angle is generally an angle w, shown in FIG. 7 between about 10° and 80°. More specifically, the acute angle is about 20-30°.

The removed area of the absorbent nonwoven web forms apertures in the absorbent nonwoven web. The apertures formed by the first and second plurality of slits has an effective length in longitudinal direction in the range between about 2 mm and about 20 mm, generally about 5 mm to about 12 mm and an effective width in lateral direction in the range between about 0.5 mm and about 10 mm, and generally about 1 mm to about 6 mm.

By providing the slitted and apertured absorbent layer in an absorbent personal care product, functional and aesthetical enhancements are provided to the absorbent personal care article. Functional enhancements include improved fluid distribution of an insulting fluid as compared to a non-slitted and non-apertured absorbent layer made from the same. In a further embodiment of the absorbent layer according to the present invention, the formation of the slits and apertures in the absorbent layer increases the distribution of defibrinated sheep blood in the longitudinal direction of the absorbent layer by 1.5 to 2 times, compared to an identical absorbent layer, but without a pattern of cuts corresponding to the pattern of slits and apertures, as measured by observing the distribution of 3 ml of defibrinated sheep blood, which have been brought into contact with the absorbent layer after 10 minutes. Although not wishing to be bound by theory, it is believed that the slits and apertures in the absorbent layer allow the absorbent layer to quickly intake and transport an insulting fluid from the top layer into the absorbent layer by the capillaries and void space created by the combination of slits and apertures and by the increase in the surface area of the absorbent layer provided by the apertures.

Other function enhancements include that the resulting absorbent article has multidirectional extensibility in the lateral and diagonal axes. As a result, the absorbent article tends to move with the user, providing a comfortable to wear absorbent article. The absorbent article, in particular, a feminine sanitary napkin or incontinence pad, will respond to the movements of a user, for example, when walking or other body motions, making the absorbent article less noticeable to a user.

From an aesthetic standpoint, by having apertures and slits in the absorbent layer, additional layer under the absorbent layer may be viewed by the user, if the additional layers are of a different color. This could convey a message to a user that the absorbent article has improved absorbency, intake capacity, comfort, breathability, protection or fit. In addition, the apertures could be used to provide color or aesthetic designs in an absorbent article in which the absorbent layer is used.

The absorbent layer may contain other additives to help control odor, such as zeolites, baking soda or other conventional odor control agents. By having the apertures and slits in the absorbent layer, the surface area of the odor control agent may be increased, thereby effectively increasing the odor control properties of the absorbent layer. Other layers of the absorbent article may also contain odor control agents. If the odor control agents are in a layer below the absorbent layer, the odors may be able to more effectively come into contact with the odor control agent due to the presence of the slits and apertures. Further, the slits and apertures may also provide a means for improving the breathability of the absorbent article and the absorbent layer, allowing air to more readily pass through the absorbent layer.

The absorbent article according to the present invention may further comprise a garment attachment system, which in one embodiment may consist of at least one adhesive strip on the surface of the liquid-impermeable backing layer 30 facing away from the wearer's body, and covering means for covering the at least one adhesive strip 32. The adhesive may be, for instance, a hot-melt adhesive or pressure sensitive adhesive. The covering means may be, for instance, a release tape, which may be made of a silicone paper. In a further embodiment of the absorbent article according to the present invention, the garment attachment system consists of two separate adhesive strips extending in the longitudinal direction of the absorbent article and either two corresponding release tapes or a single release tape comprising a dividing line formed by perforations, which allows the release tape to be easily divided into two separate release tapes, for covering the adhesive strips. The absorbent article comprising such a garment attachment system is also extensible when the perforated release tape or the two release tapes are still attached to the absorbent article. In the case of the perforated release tape, the application of tension will divide the release tape into two separate release tapes. This allows the user to perceive the extensibility of the absorbent article even without having to remove the release tape from the absorbent article.

As shown in FIG. 2, the absorbent article 10 according to the present invention may comprise additional layers positioned between the absorbent layer and the backing layer 30. The absorbent article 10 may, for instance, further comprise a transfer layer 26 for further enhancing the distribution of liquid in the horizontal direction of the absorbent article. The transfer layer 26 may, for instance, be a meltblown material, an airlaid material, a spunbond or carded web material or any other material which has been used as a transfer layer in absorbent articles. Typically, the transfer layer will have a basis weight of between 20 to 200 $g/m^2$, and generally between 70 to 110 $g/m^2$.

Additionally or instead of the transfer layer 26, the absorbent article 10 may further comprise an additional absorbent layer 28, also referred to as a storage layer, which may be prepared from cellulose fluff pulp and, optionally, superabsorbent particles or superabsorbent fibers and/or odor controlling additives. The additional absorbent layer may be in the shape of an oval pillow, shown in FIG. 2, to further increase the absorbent capacity of the absorbent article and at the same time providing wearing comfort for the user. In the alternative, the additional absorbent layer may be coextensive with the first absorbent layer 16, or slightly smaller than the first absorbent layer 15 (not shown).

As outlined above, the present invention provides an absorbent layer for use in an absorbent article having a longitudinal direction and a lateral direction, wherein the absorbent layer is made of a nonwoven absorbent material and has a plurality of slits formed therethrough. The slits are formed from a first plurality of slits with a first orientation and a second plurality of slits with a second orientation, wherein the first orientation is different from the second orientation. The first plurality of slits and the second plurality of slits are at least partially through the absorbent nonwoven web, and the second plurality of slits at least partially intersects the first plurality of slits in a manner such that where the first and second plurality of slits intersect the first and second plurality of slits combine to form openings or apertures in the absorbent nonwoven web. Each slit is formed by removing a section of the nonwoven absorbent material from the absorbent layer and simultaneously densifying the nonwoven absorbent material in the areas of the absorbent layer adjacent to the edge of the opening created by slitting the absorbent layer material, i.e. adjacent to the removed section of the slit. In the area of the absorbent nonwoven web where the first plurality of slits intersects a second plurality of slits, the second plurality of slits cuts through the absorbent nonwoven web such that a portion or at least one of the second plurality of slits cuts the absorbent nonwoven web up to and possibly beyond the first slits. In doing so, the portion of the absorbent nonwoven web which is between the first slit and the second slit is cut free from the nonwoven web, thereby causing the area between the slits to be removed from the nonwoven web. As a result, the nonwoven web has apertures formed therein.

The absorbent layer may be any suitable material for use in absorbent articles such as sanitary napkins and other disposable absorbent articles. The special slits and aperture combination in the absorbent layer, according to the present invention, can especially be formed in the above described absorbent layers discussed in connection with the absorbent articles according to the first aspect of the present invention. It should, therefore, be understood that the absorbent articles described above as the first aspect of the present invention may have the specially slitted and apertured absorbent layers according to the second aspect of the present invention and that the absorbent layers described with references to the second aspect of the present invention may be made of the materials described with reference to the absorbent layers in the absorbent articles according to the first aspect of the present application.

Figure 8A:
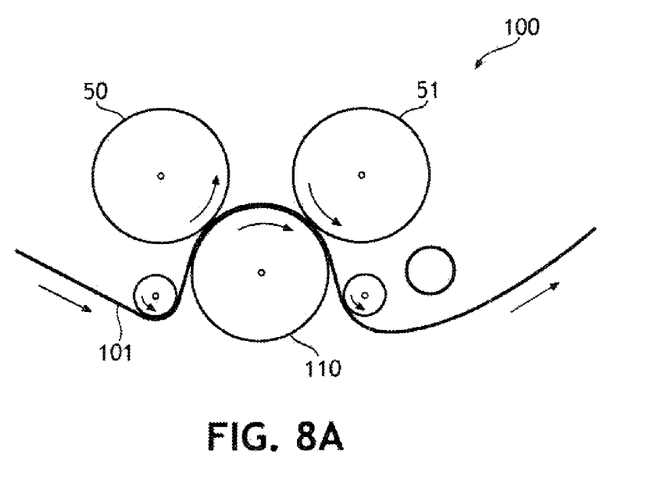
FIG. 8A shows a schematic representation of an apparatus of the present invention with two slitting rolls.
Figure 8B:
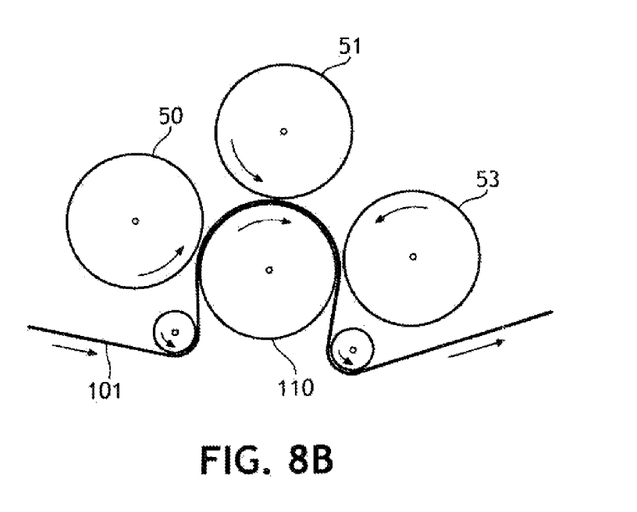
FIG. 8B shows a schematic representation of an apparatus of the present invention with more than two slitting rolls.

In another aspect of the present invention, the present invention provides an apparatus to prepare the absorbent layer having a first plurality of slits with a first orientation and a second plurality of slits with a second orientation, wherein the first orientation is different from the second orientation, the first plurality of slits and the second plurality of slits are at least partially through the absorbent nonwoven web 101, and the second plurality of slits at least partially intersects the first plurality of slits in a manner such that where the first and second plurality of slits intersect the first and second plurality of slits combine to form apertures in the absorbent nonwoven web 101. In this regard, attention is directed to FIG. 8A, which shows the apparatus of the embodiment of the present invention. The slitting and aperturing apparatus 100 has an anvil roll 110, a first cutting roll 50 and a second cutting roll 51, wherein the first cutting roll 50 and second cutting roll 51 are in communication with the anvil roll 110. By "in communication with" it is intended that the cutting rolls are close enough to the anvil roll that the motion of each of the anvil roll and the cutting rolls are essentially at the same pace, taking into account the diameter of each roll. By having the cutting rolls 50, 51 and the anvil roll 110 in communication with one another, one of the rolls can be driven by a motor (not shown) and the other rolls are turned due to the motion of the roll driven by the motor. As a result, the anvil roll and the cutting rolls can be easily driven in unison. The slitting and aperturing apparatus may have other guide rolls and other features commonly present in an anvil slitting operation. In a further embodiment of the apparatus of the present invention, there may be at least one additional cutting roll 53, shown in FIG. 8B, which is also in communication with the anvil 110. Each additional cutting roll 53 may be run in unison with the anvil roll 110 and the first and second cutting rolls 50, 51.

Figure 9A:
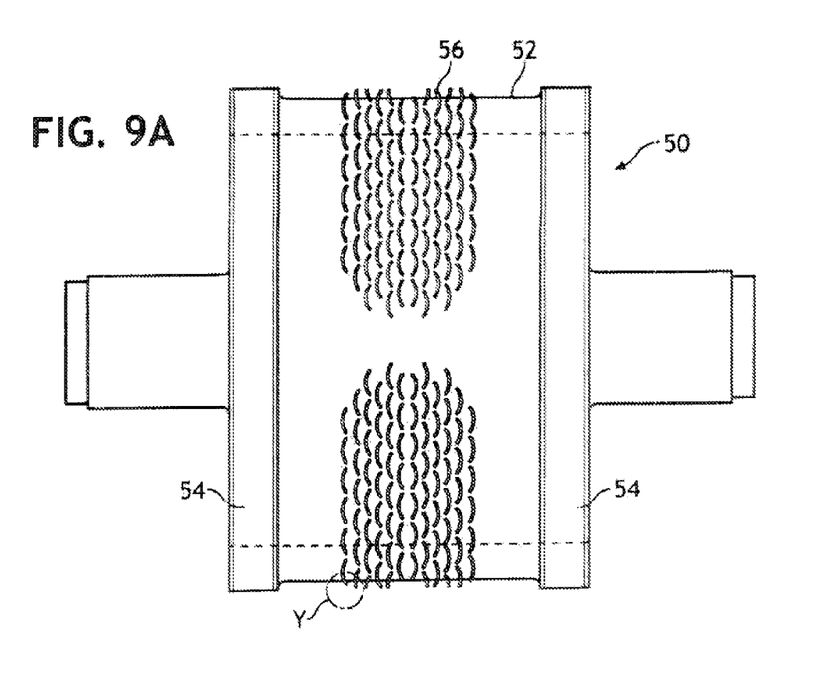
FIG. 9A shows a slitting roll usable in the process of the present invention.
Figure 9B:
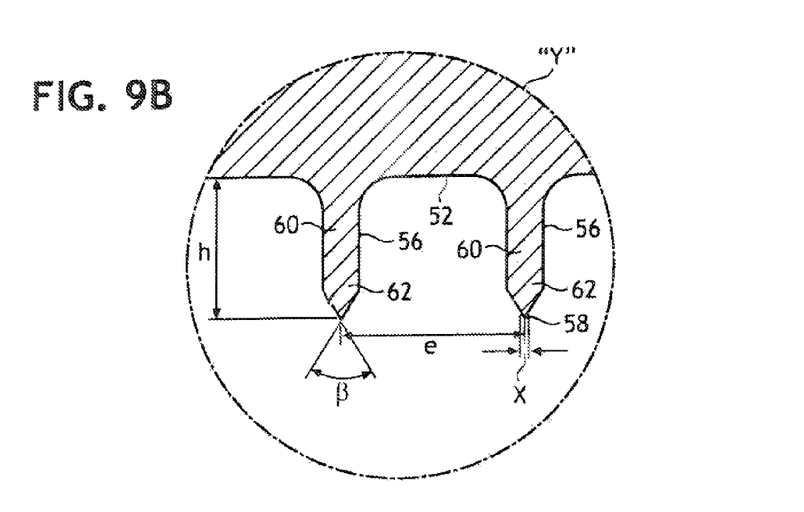
FIG. 9B shows a magnified view of the encircled region of the slitting roll of FIG. 9A.
Figure 10:
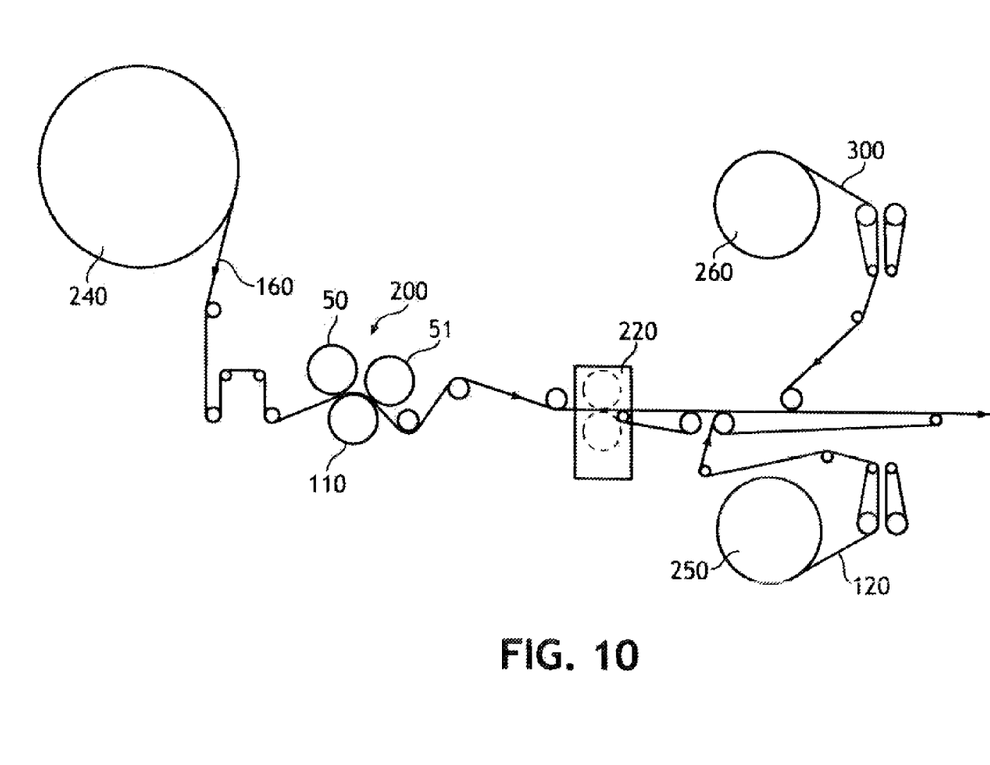
FIG. 10 shows a schematic representation of selected steps of the process for forming an absorbent article according to the present invention.

In the present invention, referring to FIG. 9, each cutting roll 50, 51 and the optional additional cutting rolls 53 has an essentially cylindrical shape and having an outer surface 52 and has a series of protrusions 56 that are capable of forming slits in a web passed between the anvil and each cutting roll. Each cutting roll of the apparatus may further have, as shown in FIG. 9, two outer, elevated rim sections 54. The cutting roll has at least one plurality of punching or cutting elements 56 for forming a pattern of slits in a web passed between the anvil roll and each cutting roll. In the case of the present invention, the web may be the absorbent layer described above. As shown in FIG. 10, each punching element may have a height h, which is the distance between the outer surface 52 and the tips 58 of the punching elements 56. The height h may be adapted for each respective web material to be cut. Each punching element comprises a base section 60 protruding from the outer surface 52 of the roller. In the embodiment shown in FIG. 9 and FIG. 10, the latter one showing a cross section of the area denoted "Y" in FIG. 9, the side walls 60 of the punching element 56 are essentially linear and extend in a direction perpendicular to the outer surface 52 of the roller 50. Extending from the base section 60 is the blade section 62 of the punching element, which has a trapezoidal cross section perpendicular to the direction in which the respective slit in the pattern is formed, and a tip 58. The trapezoidal cross section defines two parallel sides running in parallel with the outer surface 52 and two non-parallel sides, said two non-parallel sides enclosing an angle β of between 45 to 75°, preferably between 55° and 65°, and the smaller of said two parallel sides, which represents the tip 58 of the punching element. The tip will generally have a width of between 0.1 mm and 0.45 mm, depending on the material to be cut, slitted or punched. It is noted that the pattern of punching elements shown in FIG. 9 is merely exemplary and is not intended to be limiting. Other patterns of punching elements previously described may also be used, as with other patterns not specifically mentioned in the present specification that do not depart from the intention or spirit of the present invention.

At least some of the protrusions of the first cutting roll and some of the protrusions of the second cutting roll are aligned on the anvil such that at least a portion of slits cut by the first cutting roll are overlapped with at least a portion of the slits cut by the second cutting roll. As is described above, where the slits overlap, if the slits are properly aligned, the slits combine to form apertures in the web. The pattern of punching elements on the second cutting roll may be the same or different from the punching elements of the first cutting roll, where the slits desirably overlap one another. Each additional cutting roll has a series of protrusions that are capable of forming slits in a web passed between the anvil and each cutting roll.

The apparatus of the present invention provides advantages over other dual cutting apparatus. By having each of the cutting rolls in communication with the anvil roll, the anvil roll or another drive roll can be used to operate all of the rolls in the apparatus. This will ensure that the first cutting roll and the second cutting roll will be turned in unison with each other, keeping the slits cut by the first cutting roll aligned with the slits cut by the second cutting roll which provide apertures in the web. By having the cutting rolls turn in unison with a single drive roll, a high level of precision in forming slits and apertures in the webs passed through the apparatus will be achieved. The apparatus provides a less complex process than processes that conventionally form apertures, by providing a means for registering cutting patterns between the first and second cutting rolls. In addition, the apparatus of the present invention provides other advantages, including a lower cost of capital, a way to cut slits and apertures in a single apparatus, and providing a less complex apparatus for cutting slits and apertures.

The apparatus of the present invention may be used in the process according to the present invention to form the absorbent article and the absorbent layer described above. All of the materials described above, with reference to the absorbent layer of the present invention may be formed using the apparatus of the present invention. The process according to the present invention, utilizes the apparatus and includes the steps of a) providing a web; b) providing a slitting apparatus having an anvil roll, a first cutting roll and a second cutting roll; c) passing the web between the first cutting roll and the anvil to form a first plurality of slits in the absorbent nonwoven web; and d) passing the web between the second cutting roll and the anvil to form a second plurality of slits in the absorbent nonwoven web, wherein at least one slit in the second plurality of slits intersects at least one slit from the first plurality of slits such that an aperture is formed in the web. In the process of the present invention, both the first and second cutting rolls are positioned adjacent the same anvil roll. That is, the first cutting roll and the second cutting roll place slits in a web which is passed through the apparatus, including the absorbent nonwoven web of the present invention, between the first and second cutting rolls and the anvil roll. The absorbent nonwoven web of the present invention is brought into contact with the anvil roll, cut with the first cutting roll. Once cut or slitted with the first cutting roll, the web remains in contact with the anvil roll and is cut or slit with the second cutting roll. The first and second cutting rolls may be run in unison to register the first and second slits cut into the web, which can result in apertures being formed into the nonwoven web.

In a further embodiment of the process according to the present invention, the process may comprise the additional steps of d) attaching the absorbent layer to a top layer material sheet, e) laminating a backing layer material sheet to the top layer material sheet in such a manner that the absorbent layer is positioned between the top layer material layer and the backing material layer, and f) cutting the laminate of top layer material sheet, absorbent layer and backing layer material sheet into the shape of an absorbent article.

FIG. 10 shows a schematic representation of an embodiment of the process according to the present invention. Except for the use of the slitting and aperturing apparatus according to the present invention, the process may use known apparatuses and process steps commonly used in the art of producing absorbent articles, which are well known to the person skilled in the art and therefore do not require a detailed discussion.

The absorbent layer material sheet 160 is provided from supply roll 240 and transported to slitting apparatus 200. The slitting apparatus 200 contains the first slitting roll 50, a second slitting roll 51 and an avil roll 110 according to the present invention. In the slitting apparatus, patterns of slits are formed in the absorbent layer material sheet 160. From the slitting apparatus 200, the slitted absorbent layer material sheet 160 is transported to the cutting station 220, which cuts absorbent layers from the absorbent layer material sheet 160. These absorbent layers are then transported from the cutting station 220 and attached, for instance laminated, to a top layer material sheet 120, which is provided from the supply roll 250. The remaining absorbent layer material sheet can be removed separately from the cutting station using conventional techniques (not shown). To laminate the absorbent layer to the top layer material sheet 120, an adhesive may be applied to the top layer material sheet 120 before the absorbent layers are deposited on the top layer material sheet 120. Next, a backing layer material sheet 300, which is provided from supply roll 260 is laminated to the laminate of absorbent layers and top layer material sheet 120 in such a manner that the absorbent layers are positioned between top layer material sheet 120 and the backing layer material sheet 300. Again, an adhesive may be applied to the backing layer material sheet 300 to achieve the lamination.

From this laminate, absorbent articles comprising a top layer 12, absorbent layer 16 and backing layer 30 can subsequently be cut and formed. If additional layers, such as transfer layers and fluff pads are to be incorporated into the absorbent articles, additional conventional process steps would have to be incorporated into the process, by means of which these components are formed in the absorbent articles. The process may further comprise embossing steps to provide embossing lines or patterns in the absorbent articles. Furthermore, steps for forming garment attachment systems on the absorbent article, either on the backing sheet or the wing sections of the absorbent articles or both may be carried out, for instance, by an application of adhesive strips and application of corresponding release tapes.

EXAMPLES

To test the improved liquid transportation properties of the absorbent layer and the mechanical properties of the absorbent layer, an airlaid absorbent layer laminate of a spunbond support and an airlaid nonwoven web is used. The airlaid nonwoven web has a basis weight of 90 g/m$^2$ and contains about 76% by weight pulp, 15.5% bicomponent fibers, 2.5% by weight latex and 6% by weight polyethylene powder. The support layer is a 17 g/m$^2$ polypropylene spunbond support layer, which gives the absorbent layer laminate a total basis weight of about 107 g/m$^2$.

The absorbent layer laminates are slitted using the process and apparatus of the present invention described above. Two different slitting and aperturing patterns are used. One slitting and aperturing pattern is the pattern as shown in FIG. 4, which results in crescent shaped apertures and arced slits in the absorbent layer. The arced slits are about 2 mm apart in the MD and have an effective length of about 8.5 mm and an effective width in the CD of about 2 mm. The apertures formed in the absorbent layer have an effective width in the CD of about 2 mm and an effective length in the MD of about 6 mm.

A second slitting and aperturing pattern shown in FIG. 5 is used, which results in rhombus shaped apertures and V-shaped slits in the absorbent layer. The V-shaped slits are about 4 mm apart in the MD and have an effective length of about 14 mm and an effective width in the CD of about 2 mm. The apertures formed in the absorbent layer have an effective width in the CD of about 2 mm and an effective length in the MD of about 7 mm.

As a control in a comparative example, an identical nonwoven web without slits or apertures is used for comparison.

1. Fluid Handling and Wicking Properties

Each of the slitted and apertured absorbent layers and the control are tested for wicking. Each absorbent layer is placed on a liquid-impermeable sheet and 2 ml of defibrinated sheep blood obtained from OXOID, Wesel, Germany, were applied onto the central area of each absorbent layer using a pipette. After 10 minutes, an additional 1 ml of the defibrinated sheep blood is applied as a second insult onto the central area of the absorbent layer. The maximum lateral and longitudinal wicking distance of the blood in the absorbent cores is measured. Several samples of each were tested and the range of maximum longitudinal length of the resulting stain and the maximum lateral length of the resulting stain were measured. For each the wicking factor, which is the maximum longitudinal length/maximum lateral length of the stain, is calculated. The same was done for the control. The results are shown in Table 1.

TABLE 1

Calculated wicking factor ranges for each slit/aperture pattern

| Slit and aperture pattern | Range of Wicking Factors for All Samples of slit/aperture pattern | Avg. max. longitudinal length | Avg. max lateral length |
| --- | --- | --- | --- |
| Arced slits/crescent apertures | 1.44-1.65 | 97 mm | 63 mm |
| V-slits and rhombic apertures | 1.61-1.87 | 108 mm | 62 mm |
| Control (none) | 1.0-1.04 | 56 mm | 55 mm |

The above data shows that the absorbent layer having both apertures and slits according to the present invention exhibit an improved liquid transportation in the longitudinal direction of the absorbent core. The absorbent cores therefore make more efficient use of the absorbent capacity of the absorbent material. At the same time, the liquid transportation in lateral direction is only increased to a small extent. A too high transport rate in the lateral direction would increase the risk of leakage at the sides of the absorbent article. The improved liquid transportation in longitudinal direction therefore enables that more of the absorbent material present in the absorbent article is utilized before the absorbent article needs to be changed.

2. Mechanical Properties of the Absorbent Layer According to the Present Invention.

The tensile strength and elongation at tear of the absorbent layers described above in this Example and the Control-samples were measured using a conventional tensile strength machine complying to DIN 51221. The samples had a width of 50 mm and were measured with a clearance between clamps of 50 mm and a haul-off speed of 50 mm/min. Each sample is tested in the MD, the CD and 45 degrees to the MD and CD. The measurement followed essentially the procedure outlined in DIN 53857 but did not use a pre-load force. The flexural resistance of the absorbent core samples was measured according to the above mentioned circular bend procedure.

The measured values of the samples according to the present invention with the arced slits and crescent apertures and/or the v-shaped slits and rhombic apertures described above are compared below in Table 2 with those of an identical absorbent layer without any slits or apertures formed therein and the identical absorbent layer with only slits cut therein. All values are average values derived from measurement of 5 samples with the exception of the flexural resistance which compared 10 samples.

TABLE 2

Mechanical properties of the absorbent cores

| Test specimen | Arced slits/crescent apertures | V-slits and rhombic apertures | Arced slits only | V-slits only | No slits or apetures |
| --- | --- | --- | --- | --- | --- |
| Tensile strength MD (N/50 mm) | 18.8 | 16.2 | 30.0 | 21.9 | 42.6 |
| Tensile strength CD (N/50 mm) | 3.6 | 2.2 | 4.8 | 3.1 | 24.4 |
| Tensile strength at 45° (N/50 mm) | 6.5 | 3.1 | 6.7 | 4.4 | 31.2 |
| Elongation at tear MD (%) | 12.5 | 12.2 | 14.5 | 11.3 | 17.5 |
| Elongation at tear CD (%) | 34.5 | 105 | 36.5 | 108 | 23.0 |

TABLE 2-continued

Mechanical properties of the absorbent cores

| Test specimen | Arced slits/crescent apertures | V-slits and rhombic apertures | Arced slits only | V-slits only | No slits or apetures |
|---|---|---|---|---|---|
| Elongation at tear 45° (%) | 14.8 | 23.8 | 13.2 | 15.3 | 20.1 |
| Elongation at 3N CD (%) | 25.7 | —* | 19.2 | 98 | 0.8 |
| Elongation at 3N 45° (%) | 4.3 | 20.5 | 3.0 | 7.1 | 0.5 |
| Flexural resistance (N) | 0.46 | 0.29 | 0.67 | 0.43 | 0.69 |

*tore at 2.2 N.

The above data shows that the absorbent cores comprising the slits and apertures prepared in accordance with the present invention have an increased extensibility while maintaining a sufficient flexural resistance and tensile strength in MD for processing the material in a process for making absorbent articles, as compared to absorbent layers only slitted or absorbent layers not slitted.

While the present invention has in the above been described with special reference to specific embodiments and examples, those skilled in the art will readily appreciate that many modifications are possible in the exemplary embodiments without materially departing from the novel teachings and advantages of this invention. Accordingly, all such modifications are intended to be included within the scope of this invention as defined in the following claims. It should be further noted that any patents, applications or publications referred to herein are incorporated by reference in their entirety.

What is claimed is:

1. A process for preparing an aperture web, said process comprising:

a) providing a web of a material comprising a top layer, a backing layer, and an absorbent layer positioned between the top layer and the backing layer, wherein said absorbent layer comprises an absorbent nonwoven web;

b) providing a slitting apparatus comprising an anvil roll, a first cutting roll and a second cutting roll, wherein the first cutting and second cutting rolls are in communication with the anvil roll;

c) passing the web between the first cutting roll and the anvil to form a first plurality of slits in the web; and d) passing the web between the second cutting roll and the anvil to form a second plurality of slits in the web, wherein at least one slit in the second plurality of slits intersects at least one slit from the first plurality of slits such that the area of the web between the intersecting slits is cut free from the web, thereby forming at least one aperture in the web, the aperture having an effective length in longitudinal direction in the range between about 2 mm and about 20 mm and an effective width in lateral direction in the range between about 0.5 mm and about 10 mm, wherein the absorbent nonwoven web is removed at the at least one aperture.

2. The process according to claim 1, wherein the first cutting roll has a series of protrusions which are non-linear and the first plurality of slits are non-linear.

3. The process according to claim 2, wherein the second cutting roll has a series of protrusions which are non-linear and the second plurality of slits are non-linear.

4. The process according to claim 1, wherein the first cutting roll and the second cutting roll are driven in unison with the anvil roll.

5. The process according to claim 1, further comprising providing at least one additional cutting roll which is in communication with the anvil roll and passing the web between the at least one additional cutting roll and the anvil roll.

* * * * *